United States Patent
Velasco Varo et al.

(10) Patent No.: US 7,544,823 B2
(45) Date of Patent: Jun. 9, 2009

(54) SUNFLOWER SEEDS WITH HIGH DELTA-TOCOPHEROL CONTENT

(75) Inventors: Leonardo Velasco Varo, Cordova (ES); José M. Fernández Martínez, Cordova (ES)

(73) Assignee: Consejo Superior De Investigaciones Cientificas, Madrid (ES)

( * ) Notice: Subject to any disclaimer, the term of this patent is extended or adjusted under 35 U.S.C. 154(b) by 136 days.

(21) Appl. No.: 11/245,991

(22) Filed: Oct. 7, 2005

(65) Prior Publication Data

US 2006/0112450 A1    May 25, 2006

Related U.S. Application Data

(63) Continuation of application No. PCT/ES2004/070019, filed on Apr. 7, 2004.

(51) Int. Cl.
*C07C 51/43* (2006.01)
*C07C 57/00* (2006.01)

(52) U.S. Cl. ........................ 554/224; 554/227

(58) Field of Classification Search ............... None
See application file for complete search history.

(56) References Cited

OTHER PUBLICATIONS

Warner et al., JAOCS, vol. 67, No. 11, pp. 827-831, 1990.*
F.B. Padley et al., The Lipid Handbook, Second Edition, Occurrence and Characteristics of Oils and Fats, 47-223, (1994).
G. Pongracz et al., Fat. Sci. Technol., 97. Jahrgang Nr. 3, 90-104, (1995).
Y. Demurin, Hella, 16, Nr. 18, 59-62 (1993).
L. Velasco et al., Crop Science, vol. 44: 362 (2004).
Y. Demurin et al., Plant Breeding, vol. 115: 33-36 (1996).
F. D. Goffman et al., Fett/Lipid, 101, Nr. 4. 142-145 (1999).
Mutation Analysis and Selective Use of Tocopherol Biosynthesis Specifics In Sunflower, In Scientific and Technical Bulletin of All-Russia Scientific Research Institute of Oil-Bearing Crops, Issue 124, Krasnodar (2001).

* cited by examiner

*Primary Examiner*—Deborah D Carr
(74) *Attorney, Agent, or Firm*—Klauber & Jackson

(57) ABSTRACT

The present invention relates to sunflower seeds which have been genetically modified through two artificial induction cycles of mutations followed in each case by processes for the identification of mutant individuals which have the desired character. The disclosed seeds are characterised in that they contain between 26% and 80% of the tocopherols as delta-tocopherol. This high delta-tocopherol production is determined by the genotype of the seeds which have been modified to this effect, and is always obtained independently of the culture conditions, thereby obtaining an inheritable character. Today, sunflower seeds producing such high levels of delta-tocopherol do not exist. Genetically modified sunflower plants which produce through self-fertilization seeds with high delta-tocopherol levels and the oil with high natural delta-tocopherol concentration, extracted from the seeds, are also objectives of the present invention.

1 Claim, No Drawings

SUNFLOWER SEEDS WITH HIGH DELTA-TOCOPHEROL CONTENT

RELATED APPLICATIONS

The present application is a Continuation of co-pending PCT Application No. PCT/ES2004/070019, filed Apr. 7, 2004, which in turn, claims priority from Spanish Application Serial No. P200300859, filed Apr. 10, 2003. Applicants claim the benefits of 35 U.S.C. §120 as to the PCT application and priority under 35 U.S.C. §119 as to said Spanish application, and the entire disclosures of both applications are incorporated herein by reference in their entireties.

SECTOR OF THE ART

The invention comes within the sector of agriculture, concerning seeds with a high delta-tocopherol content. The oil extracted from the seeds has high oxidation stability and is optimum for food and industrial uses (biofuels and lubricants). This oil and its by-products can be used for extraction of delta-tocopherol, with numerous applications in the food, cosmetic and pharmaceutical industries.

STATE OF THE ART

Tocopherols are the main natural components with antioxidant properties present in seed oils. As they are liposoluble, they pass into the oil during the extraction process and exert an important antioxidant activity, both in the bottled oil and in foods containing vegetable oil (F. B. Padley et al., 1994; Occurrence and characteristics of oils and fats. In The Lipid Handbook, ed. F. D. Gunstone, J. L., Harwood and F. B. Padley, London; Chapman & Hall, pp 47-223). Of the four types of existing tocopherols (alpha-, beta-, gamma and delta-tocopherol), the maximum antioxidant activity in vitro, in other words, outside the human body, corresponds to beta-, gamma- and delta-tocopherol, while alpha-tocopherol displays notably lower in vitro activity than the other three tocopherols (G. Pongracz et al., Tocopherole, Antioxidanten der Natur. Fat Science and Technology 97; 90-104, 1995).

Standard sunflower seeds present a tocopherols fraction dominated by alpha-tocopherol, which represents around 95% of total tocopherols, the rest consisting of beta-tocopherol and gamma-tocopherol, which are present in proportions of less than 5% of total tocopherols (F. B. Padley et al., 1994 cited work). Owing to the predominance of alpha-tocopherol in sunflower seeds, its oil displays lower protection towards oxidation than other vegetable oils extracted from seeds containing higher proportions of beta-, gamma- and/or delta-tocopherol, which exert greater antioxidant activity in vitro. Table 1 shows the tocopherol composition of the main seed oils.

TABLE 1

Average composition of tocopherols in the main seed oils

| Oil | % Tocopherol | | | |
| --- | --- | --- | --- | --- |
|  | Alpha | Beta | Gamma | Delta |
| Cotton | 43 | 2 | 55 | 0 |
| Peanut | 44 | 2 | 52 | 2 |
| Rapeseed | 26 | 9 | 64 | 1 |
| Safflower | 90 | 8 | 2 | 0 |
| Sunflower | 95 | 4 | 1 | 0 |
| Linseed | 1 | 0 | 99 | 0 |
| Maize | 20 | 3 | 73 | 4 |
| Castor | 6 | 6 | 23 | 65 |
| Soya | 6 | 1 | 66 | 27 |

The predominance of alpha-tocopherol in sunflower seeds is practically universal, and just four lines of sunflower have been described presenting modified levels of tocopherols, which can be grouped into two classes:

a) High content in gamma-tocopherol. This concerns two lines possessing more than 85% of tocopherols in the form of gamma-tocopherol, the rest being alpha-tocopherol. One of them, known as LG-17, was developed in Russia (Y. Demurin, Genetic variability of tocopherol composition in sunflower seeds, Helia 16:59-62, 1993), while the second was developed in Spain and was known as T2100 (L. Velasco et al., Registration of T589 and T2100 sunflower germplasms with modified tocopherol profiles, Crop Science, in press).

b) Average content in beta-tocopherol. This concerns two lines possessing between 30% and 50% of tocopherols in the seed in the form of beta-tocopherol, the rest being alpha-tocopherol. One of them, known as LG-15, was developed in Russia (Y. Demurin, cited work), while the second, known as T589, was developed in Spain (L. Velasco et al., in press, cited work).

By means of crossing between the lines LG-15 and LG-17, Russian and Yugoslav researchers obtained recombinants with slightly increased levels of delta-tocopherol, the maximum level obtained of that tocopherol being 25% of all tocopherols present in the seed (Y. Demurin et el. Genetic variability of tocopherol composition in sunflower seeds as a basis of breeding for improved oil quality. Plant Breeding 115:33-36, 1996). To summarise, the maximum levels of individual tocopherols existing today in sunflower seeds are:

95% alpha-tocopherol (natural composition)
50% beta-tocopherol
95% gamma-tocopherol
25% delta-tocopherol

EXPLANATION OF THE INVENTION

One of the objects of the present invention is sunflower seeds with a high content of delta-tocopherol, which present between 26% and 80% of total tocopherols in the form of delta-tocopherol, and the following contents of other tocopherols: between 0.5% and 45% of total tocopherols in the form of alpha-tocopherol, between 0% and 60% of total tocopherols in the form of beta-tocopherol, between 0% and 70% of total tocopherols in the form of gamma-tocopherol. Some of these seeds present a delta-tocopherol content that is always greater than 50%, 65% and 75% of total tocopherols in the seeds. The character of high delta-tocopherol content of sunflower seeds is inheritable (being self-fertilised) and is expressed stably, independently of the environmental conditions.

Another object of this invention is the sunflower oil extracted from these seeds, by any procedure, and which naturally, without any kind of external addition, presents a high delta-tocopherol content (26-80% of total tocopherols in the form of delta-tocopherol).

Also constituting another object of the present invention are sunflower plants (*Helianthus annus* L.) which, being self-fertilised, produce seeds displaying a high delta-tocopherol content (26-80% of total tocopherols).

DETAILED DESCRIPTION OF THE INVENTION

The present invention refers to a germplasm of sunflower (*Helianthus annus* L.) characterised by possessing a high delta-tocopherol content in the seeds. This tocopherol represents between 26% and 80% of total tocopherols in the seeds. These high levels of delta-tocopherol are not produced by sunflower plants in nature and have been obtained by means of a complex process consisting of two artificial induction cycles of mutations followed by identification of mutant plants and fixing of the mutated character. The high delta-tocopherol content that is the object of this invention is inheritable and is always produced independently of the culture conditions.

In order to obtain genetically modified plants whose seeds possess a high concentration of delta-tocopherol, a lengthy process of genetic improvement has been carried out aimed at genetically altering the biosynthetic route of tocopherols. This process has consisted of four stages: (1) Induction of artificial mutations in seeds of a standard variety of sunflower; (2) Identification of individuals with alterations in the biosynthetic route of tocopherols as a result of induced mutations and fixing of the mutated characters; (3) New induction process for artificial mutations on individuals which have already displayed a first level of alteration in the biosynthetic route of tocopherols; (4) Identification of individuals with alterations in the biosynthetic route of tocopherols different from the alterations displayed by the starting individuals, followed by fixing of the new mutant character.

The first process of mutagenesis or artificial induction for mutations consisted of treating the seeds of a standard variety of sunflower with a product having mutagenic properties, in other words, one capable of inducing mutations in the plant's DNA. Owing to the low frequency of mutations to be expected in the genes responsible for the biosynthetic route of tocopherols following the mutagenic treatment, this was followed by a process of non-destructive analysis of the tocopherol composition in several thousands of individual seeds.

If the detected mutations are to have any commercial utility, they have to be inheritable and be expressed independently of the environmental conditions in which the plants are cultivated. For this reason, a selection process was conducted aimed at fixing the mutant characters and verifying their stability under different environmental conditions. Following this process, several of the initially detected mutations were rejected, while one mutant with a high content of gamma-tocopherol (95% of total tocopherols present in the seeds) was fixed. This mutant, known as IAST-1, demonstrated that it responded to a different genetic base from that possessed by other lines with a high content in gamma-tocopherol. So, while the crossings of the lines LG-17 and T2100 with lines of standard composition in tocopherol produce F2 progenies which do not segregate for intermediate levels of gamma-tocopherol (Demurin et al., cited work; L. Velasco and J. M. Fernández-Martínez, Identification and genetic characterisation of new sources of beta- and gamma-tocopherol in sunflower germplasm, Helia, in press), the F2 progenies coming from crosses between the mutant IAST-1 and lines of standard composition in tocopherols segregated widely for intermediate levels of gamma-tocopherol.

After the genetic isolation of the IAST-1 mutant, a second process of mutagenesis was carried out on the seeds of this mutant, with the aim of generating an additional variation for high levels of other tocopherols. This second cycle of mutagenesis was likewise followed by an analytical process at the large scale in order to identify mutants, along with a process of fixing of mutants and confirmation of their expression independently of the culture conditions. In this second cycle of mutagenesis, the mutant forming the objective of this invention was identified and fixed, and is characterised in that its seeds contain high concentrations of delta-tocopherol, between 26% and 80% of total tocopherols in the seeds. This high proportion of delta-tocopherol in the seeds is an inheritable character and is expressed stably independently of the culture conditions of the plants.

MODE OF EMBODIMENT OF THE INVENTION

First Mutagenesis Cycle

Sunflower seeds of the population variety Peredovik, with a tocopherols composition in the seeds consisting of 96% alpha-tocopherol, 3% beta-tocopherol and 1% gamma-tocopherol, were soaked in distilled water for 4 hours at a temperature of 20° C. After that, the seeds were transferred to a solution of the mutagenic agent ethyl methylsulphonate (EMS) at a concentration of 70 mM in a 0.1 M phosphate buffer at pH 7.0 for 2 hours, with constant stirring at 60 rpm. Following the mutagenic treatment, the seeds (M1 generation) were washed for 16 hours with running water and then sown in the field.

The M1 plants were harvested individually and their seeds (M2 generation) were individually analysed for tocopherol composition by means of high performance liquid chromatography (HPLC), following the protocol developed by F. Goffman et al. (Quantitative determination of tocopherols in single seeds of rapeseed [*Brassica napus* L.]. Fest/Lipid 101: 142-145, 1999). Out of a total of 1080 M1 plants that were analysed, one of them displayed segregation for high levels of gamma-tocopherol, with a maximum content of 95% of total tocopherols in the form of gamma-tocopherol. Seeds with these levels of gamma-tocopherol produced plants which expressed the character uniformly. By crossing plants coming from seeds with 95% gamma-tocopherol with plants of standard varieties of sunflower, a wide segregation was observed for the gamma-tocopherol content in F2 seeds, which included levels of gamma-tocopherol intermediate between both parents. This very wide segregation was completely unexpected, given that materials with similar levels of gamma-tocopherol developed previously (Demurin et al., cited work; L. Velasco and J. M. Fernández-Martínez, cited work) had not produced any segregation for intermediate levels of gamma-tocopherol after being crossed with standard varieties of sunflower. The mutant thus obtained was named IAST-1.

Second Mutagenesis Cycle

Sunflower seeds of the mutant IAST-1, with a tocopherols composition in the seeds consisting of 5% alpha-tocopherol and 95% gamma-tocopherol, were soaked in distilled water for 4 hours at a temperature of 20° C. After that, the seeds were transferred to a solution of the mutagenic agent sodium azide at a concentration of 4 mM in a 0.1 M sodium citrate buffer at pH 3.0 for 2 hours, with constant stirring at 60 rpm. Following the mutagenic treatment, the seeds (M1 generation) were washed for 16 hours with running water and then sown in the field.

The M1 plants were harvested individually and their seeds (M2 generation) were individually analysed for tocopherol composition by means of high performance liquid chromatography (HPLC), following the protocol developed by F.

Goffman et al. (cited work). Out of a total of 1240 M1 plants that were analysed, one of them displayed segregation for high levels of delta-tocopherol, with a maximum content of 55% of total tocopherols in the form of delta-tocopherol. Seeds with these levels of delta-tocopherol produced plants which expressed the character uniformly, with delta-tocopherol concentrations of between 26% and 80% of total tocopherols present in the seeds. These levels were maintained in successive generations. The new mutant line of sunflower whose seeds produced delta-tocopherol levels of between 26% and 80% of total tocopherols was named IAST-3.

The invention claimed is:

1. A modified sunflower oil with a high delta-tocopherol content from 26% to 80% relative to total tocopherols extracted from sunflower seeds with said high delta-tocopherol content, wherein said oil, naturally, without any kind of external addition, has said delta-tocopherol content.

* * * * *